United States Patent [19]

Yu

[11] Patent Number: 4,845,277

[45] Date of Patent: Jul. 4, 1989

[54] METHOD OF PREPARING DIALKOXYBENZOIC ACID

[75] Inventor: Lin-Chen Yu, Allison Park, Pa.

[73] Assignee: Mine Safety Appliances Company, Pittsburgh, Pa.

[21] Appl. No.: 234,524

[22] Filed: Aug. 22, 1988

[51] Int. Cl.$^4$ .............................................. C07C 51/15
[52] U.S. Cl. ..................... 562/423; 562/473
[58] Field of Search .................. 562/423, 473

[56] References Cited

U.S. PATENT DOCUMENTS 2,816,918  12/1957  Wynkoop et al. .................. 562/423
4,590,291  5/1986  Böshagen et al. .................. 562/473
4,730,083  3/1988  Pastor et al. ........................ 562/423

FOREIGN PATENT DOCUMENTS 661555   6/1938  Fed. Rep. of Germany.
0104034  6/1985  Japan.
2010043  1/1987  Japan.

Primary Examiner—Paul J. Killos

[57] ABSTRACT

2,6-dialkoxybenzoic acid is made by direct metalation of 1,3-dialkoxybenzene by potassium. The metalated dialkoxybenzene is carbonated and acidified to form the dialkoxybenzoic acid.

6 Claims, No Drawings

METHOD OF PREPARING DIALKOXYBENZOIC ACID

This invention relates to the preparation of dialkoxy benzoic acid and more particularly to their preparation by direct metalation of 1,3-dialkoxybenzene.

BACKGROUND OF THE INVENTION

Dialkoxy benzoic acids have been prepared by metalation of 1,3-dialkoxybenzene acid with butyl lithium, Chem. Abstracts 95: 132423m; butyl lithium and ethyl lithium, U.S. Pat. No. 4,399,078; t-butyl sodium, Chem Abstracts 86: 42548r; and phenyl sodium, Japanese Published Application No. 68 22,969 (Chem Abst. 70: 77600y). These procedures require multiple reaction steps of first forming the metal organic reactant and then reacting it to metalate the dialkoxy benzene. The metalated dialkoxybenzene is carbonated and acidified to form benzoic acid.

BRIEF DESCRIPTION OF THE INVENTION

It is an object of this invention to provide a method for making dialkoxy benzoic acid comprising the metalation of 1,3-dialkoxybenzene by direct reaction with potassium metal.

In accordance with this invention dispersed potassium and 1,3-dialkoxybenzene are contacted in the presence of an amine solvent and an electron acceptor reactive with potassium such as α-methylstyrene, whereby the dialkoxybenzene is metalated, and the reaction mixture is carbonated and acidified in a conventional manner to precipitate the dialkoxy benzoic acid.

DETAILED DESCRIPTION OF THE PREFERRED EMBODIMENT

The reaction of the invention is represented by the equation

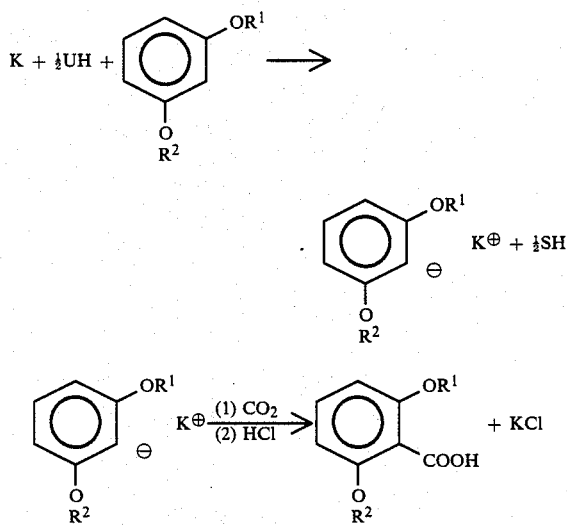

where $R^1$ and $R^2$ are independently a lower alkyl radical, suitably containing up to 5 carbon atoms. UH is an electron acceptor reactive with potassium to form a free radical intermediate, suitably conjugated unsaturated hydrocarbons such as, for example styrene, α-methyl styrene, diisopropenyl benzene or biphenyl, or a fused ring aromatic compound having from 2 to 5 fused rings with or without substituent alkyl groups, such as, for example, naphthalene, phenanthrene, anthracene, acenaphthene, fluorene and pyrene. A substantially stoichiometric amount of electron acceptor is used, that is, one-half the molar quantity of potassium. If the electron acceptor is polymerizable, such as methyl styrene, excess of stoichiometric is to be avoided. SH is the saturated hydrocarbon corresponding to the electron acceptor used.

The dialkoxybenzene is also used in substantially stoichiometric amounts, that is one mol for each mol of potassium.

The reaction is carried out in a tertiary amine solvent, suitably a trialkyl amine, cyclic amine or tetraalkylethylenediamine or mixtures thereof, such as, for example, triethylamine, tetramethylethylenediamine, or 1-methylpyrollidine.

The reaction proceeds readily at slightly elevated temperatures, suitably 60°–80° C. Temperatures above about 100° C. should be avoided to avoid decreased yield and reaction rates are very slow at temperatures as low as room temperature.

In an illustrative example of the invention, a three-necked, 500 ml. Morton flask is equipped with a mechanical stirrer, thermometer, reflux condenser and 60 ml. pressure equalizing funnel. 3.75 g. of potassium, 140 ml. triethylamine and a drop of a potassium dispersing reagent (chlorobenzene) was charged to the flask under nitrogen and the potassium was dispersed at 70° C. A solution of α-methyl styrene (5.67 g.), 1,3-dimethoxybenzene (12.06 g.) and tetramethylethylenediamine (15 ml.) in triethylamine (20 ml.) was added dropwise over a period of 69 minutes. The mixture was stirred at 70° C. for three hours after the addition. The entire reaction mixture was quenched and carbonated by pouring it over crushed dry ice (456 g.) and then allowed to warm to room temperature. The volatile components were removed from the carbonated mixture with a rotary evaporator and the resultant solids were partitioned between diethyl ether (30 ml.) and water which was extracted with diethyl ether (4 times, 30 ml.) The aqueous layer was acidified with concentrated hydrochloric acid to pH 1. The resultant precipitate, water washed and air dried, was 2,6-dimethoxybenzoic acid (13.56 g.).

I claim:

1. A method of preparing 2,6-dialkoxybenzoic acid comprising the step of metalating 1,3-dialkoxybenzene by reaction of 1,3-dialkoxybenzene, where each alkoxy group independently contains up to 5 C. atoms, potassium and an electron acceptor reactive with potassium to form a free radical intermediate in a tertiary amine solvent.

2. A method of claim 1 in which the metalated dialkoxybenzene is treated with carbon dioxide and an acid to form 2,6-dialkoybenzoic acid.

3. A method of claim 1 in which the electron acceptor is an unsaturated hydrocarbon.

4. A method of claim 3 in which the electron acceptor is α-methyl styrene.

5. A method of preparing 2,6-dialkoxybenzoic acid comprising the steps of metalating 1,3-dialkoxybenzene by reaction of 1,3-dialkoxybenzene, potassium and an electron acceptor reactive with potassium to form a free radical intermediate in substantially molar proportions of 1:1:½, in a tertiary amine.

6. A method of preparing 2,6-dimethoxybenzoic acid comprising the steps of metalating 1,3-dimethoxybenzene by reaction of 1,3-dimethoxybenzene, potassium and an electron acceptor reactive with potassium to form a free radical intermediate in a tertiary amine.

* * * * *